United States Patent [19]

Muto

[11] 4,169,479
[45] Oct. 2, 1979

[54] ELONGATED, TAPERED FLEXIBLE FRONT GUIDE FOR ELECTRICAL CATHETERS AND METHOD OF USE

[76] Inventor: Rudolph Muto, 24 William St., Andover, Mass. 01810

[21] Appl. No.: 913,558

[22] Filed: Jun. 8, 1978

Related U.S. Application Data

[63] Continuation-in-part of Ser. No. 771,526, Feb. 24, 1977, abandoned.

[51] Int. Cl.² .................................................. A61N 1/04
[52] U.S. Cl. .................................... 128/419 P; 128/784
[58] Field of Search .............. 128/404, 419 P, 419 D, 128/349 R

[56] References Cited

U.S. PATENT DOCUMENTS

| | | | |
|---|---|---|---|
| 2,221,138 | 11/1940 | Hendrickson | 128/349 R |
| 3,516,412 | 6/1970 | Ackerman | 128/419 P |
| 3,664,347 | 5/1972 | Harmjanz | 128/404 |
| 3,837,347 | 9/1974 | Tower | 128/404 |
| 3,890,977 | 6/1973 | Wilson | 128/404 |
| 3,939,843 | 2/1976 | Smyth | 128/404 |
| 3,995,623 | 12/1976 | Blake et al. | 128/404 |

*Primary Examiner*—William E. Kamm
*Attorney, Agent, or Firm*—Pearson & Pearson

[57] ABSTRACT

An endocardial lead, includes an elongated, tapered guide of non-conductive plastic in front of the exposed metal electrode which normally would form the free terminal tip of the lead. The tapered front guide eases the insertion of the catheter into a vein, and flexes into a curve which approaches the right angular when engaging the wall of the right ventricle chamber of the heart while positioning the exposed metal electrode in the apex of the chamber. The guide thus prevents the electrode from piercing the wall and its angularly bent or curved configuration tends to prevent dislodgement of the electrode from the apex.

8 Claims, 4 Drawing Figures

ELONGATED, TAPERED FLEXIBLE FRONT GUIDE FOR ELECTRICAL CATHETERS AND METHOD OF USE

RELATED APPLICATIONS

This application is a continuation-in-part of my application Ser. No. 771,526 filed Feb. 24, 1977, now abandoned.

BACKGROUND OF THE INVENTION

The conventional endocardial lead, much used with cardiac pacemakers, has one end electrically connected into a socket in the pacemaker and has a tantalum wire sleeved within a silicone tube for electrical connection to a conductive tip, or exposed electrode.

The conventional electrode of an endocardial lead is of rigid, electrically conductive, metal, and may be of ball shape. Because such conventional electrodes have been relatively blunt at the leading tip, insertion thereof into a vein and threading the endocardial lead along the vein into the ventricle chamber of the heart has been somewhat difficult. It is desirable for the electrode to be inserted until it is in the apex of the right ventricle chamber of the heart. Occasionally the conventional electrode has pierced the wall of the chamber or has been inadvertently drawn rearwardly away from its apex position.

It has heretofore been proposed as in U.S. Pat. No. 3,664,347 to Harmjanz of May 23, 1972, to provide a portion of the filament of an endocardial lead which extends beyond the electrode, thereby forming a flexible tail section that helps to hold the electrode at a desired position within the heart. However, the lead is "bi-polar" rather than "unipolar," so that intimate contact of the exposed surface of a single electrode is not required and the bi-polar lead can float in the heart without touching the surface of the heart, while being anchored through a valve into a lung.

It has been my experience that attempting to follow such teaching with a uni-polar lead may cause terminal vibration, or drilling, action giving rise to bruises and that a sliding contact is more desirable.

A bi-polar lead is disclosed in U.S. Pat. No. 4,046,151 to Rose of Sept. 6, 1977, the tip having a corkscrew for penetration into the wall of the heart, thereby risking infection, fibrosis and entailing difficulty in removal.

In U.S. Pat. No. 4,033,357 to Helland of July 5, 1977 prongs, or tines are provided to lodge the tip of a bipolar lead in the trabeclae of the right ventricle of the heart.

SUMMARY OF THE INVENTION

In this invention, an elongated, tapered front guide of non-conductive, inert, plastic, such as silicone, is integrally affixed to the free terminal end of a uni-polar endocardial lead forwardly beyond the single blunt exposed metal electrode.

The guide has a base portion proximate the electrode which forms what I call an "elbow joint" in that it is of predetermined softness, or of predetermined reduced diameter, forming a neck, to bend easily, without substantial resistance, into a curve or bend which is substantially right angular in configuration. From the base portion of predetermined high flexibility, the guide is of "rat tail" configuration tapering from a portion of enlarged diameter for about one or two inches to a terminal tip portion of reduced diameter, the softness increasing progressively toward the tip but the tip being of increased hardness to more easily be introduced into a vein.

The elongated taper and pointed tip enable it to be easily inserted in a vein and threaded along the vein into the right ventricle chamber. Upon engaging a barrier such as the chamber wall forming part of the apex, the tapered, flexible resilient guide bends and flexes into a curve with its base portion of high bendability, definning almost a right angle bend, or elbow bend while locating the metal electrode accurately in the apex. The generally right angular bend of the guide and its "rattail" shape, tend to make it what I call "splintered" in that it does not easily pull out again or become displaced due to its curl, or hook, and the easy bendability of the elbow not tending to spring it back to its normal linear configuration. The point of the guide desirably reaches up to the mid-height of the ventricle, when the single, exposed electrode is in the apex, so that it is at least one inch in length and preferably about two inches in length.

DESCRIPTION OF THE PREFERRED EMBODIMENT

Figure 1:
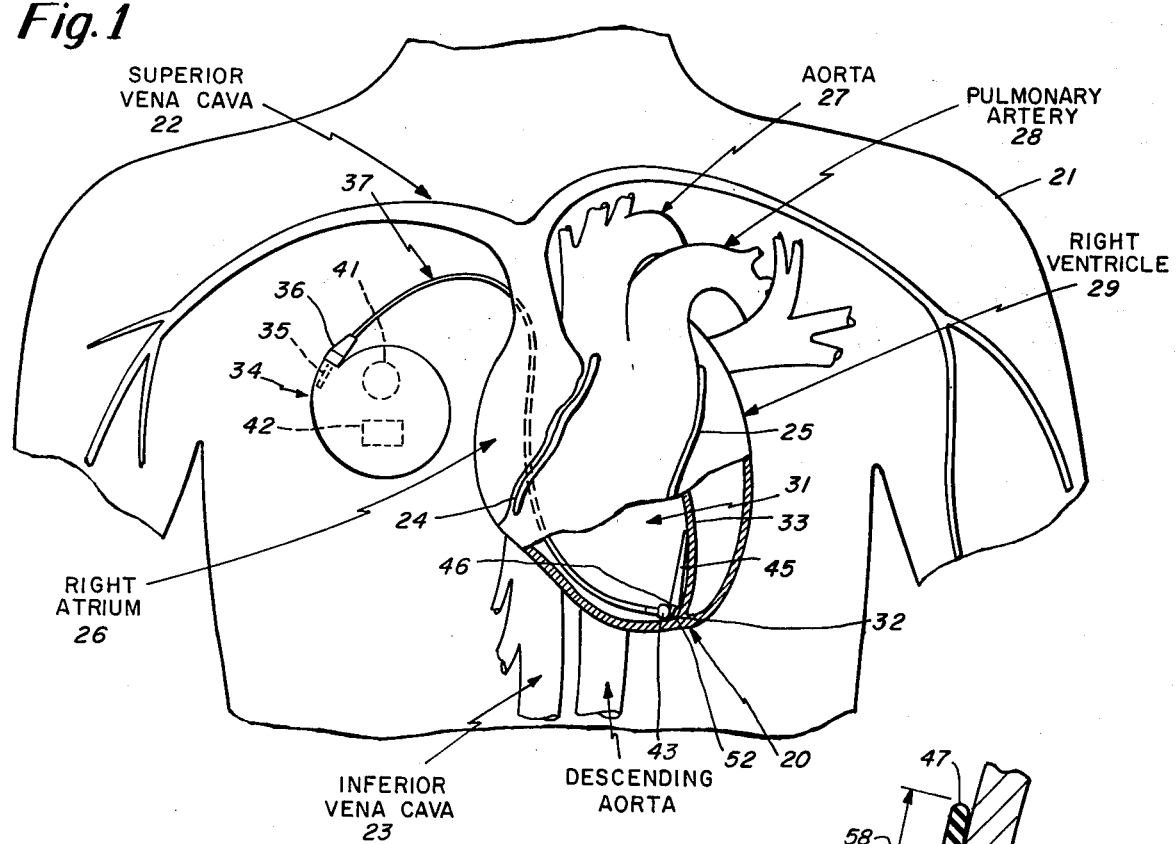
FIG. 1 is a fragmentary front elevation of the chest area of a human, showing schematically the endocardial lead and front guide of the invention in place.
Figure 2:
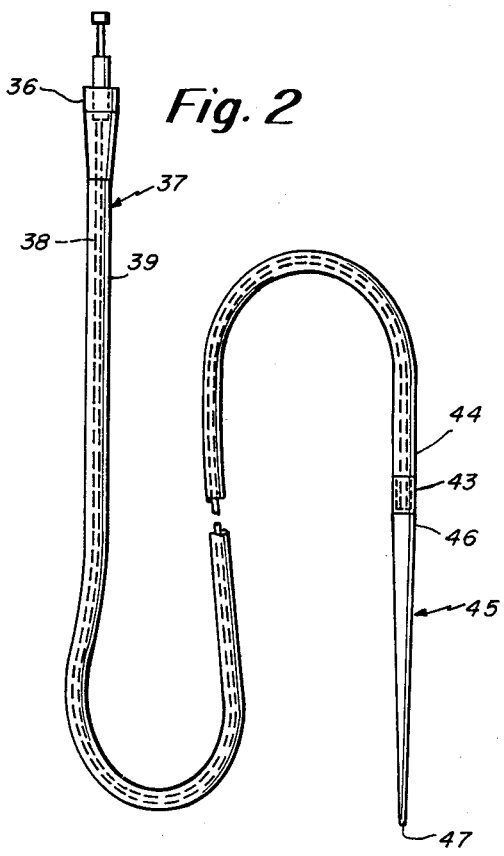
FIG. 2 is a front elevation, on an enlarged scale of the preferred embodiment of the lead of the invention.

In FIG. 1 the heart 20 of a human being 21 is shown schematically to have a superior vena cava 22, an inferior vena cava 23, a right coronary artery 24, a left coronary artery 25, a right atrium 26, an aorta 27, a pulmonary artery 28 and a right ventricle 29 with a chamber 31 having an apex 32 and a chamber wall 33.

A cardiac pacemaker 34 is shown in place in a pocket in the skin, the pacemaker having an endocardial lead connecting socket 35 for receiving one end 36 of an endocardial lead, 37 of the uni-polar type. The endocardial lead 37 includes a wire 38, usually of tantalum, sleeved within a tube 39, usually of silicone, and electrically connecting the power supply 41 and printed circuitry 42 of the pacemaker 34 to the exposed, metal, electrically-conductive electrode 43 proximate the other end 44 of the lead 37.

In this invention an elongated, tapered front guide 45, of flexible, resilient, inert, non-conductive material such as silicone is integrally affixed at 46 at the end 44 of endocardial lead 37 to extend in front of the electrode 43 for at least an inch and preferably for about two inches beyond the electrode.

Figure 3:
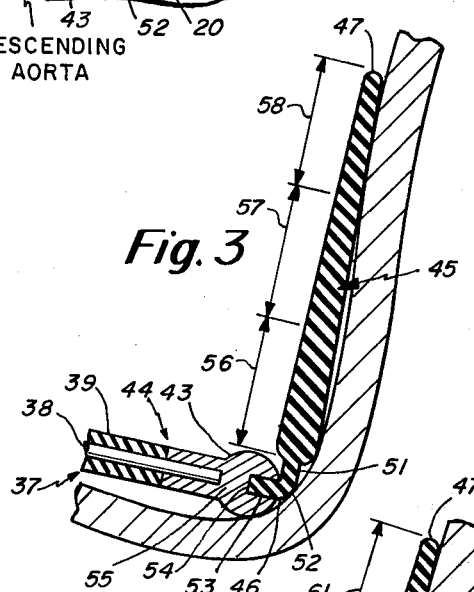
FIG. 3 is a fragmentary, front elevation, on a still further enlarged scale and in half section showing the tapered, flexible guide of the lead engaging a barrier such as the wall of a ventricle chamber; and bent through an angle of about ninety degrees.

In FIG. 3 the electrode 43 is of the exposed ball type and the front guide 45 has a neck 51 of reduced diameter and high bendability and high flexibility forming a freely bendable "elbow joint" at 52 and having the portion 53 inserted in a hole 54 in the ball 55 and anchored therein. The guide 45 then bulges outwardly in the zone 56 and tapers uniformly therefrom in a gradually decreasing cross sectional area to the pointed free terminal tip 47, which is of minute diameter. The solid silicone material of guide 45, in zone 56 is of predetermined softness and bendability which increases along the intermediate zone 57 until the zone 58, proximate the terminal tip 47, wherein the hardness increases and the bendability decreases so that the tip is relatively stiff to enable penetration into a vein.

Figure 4:
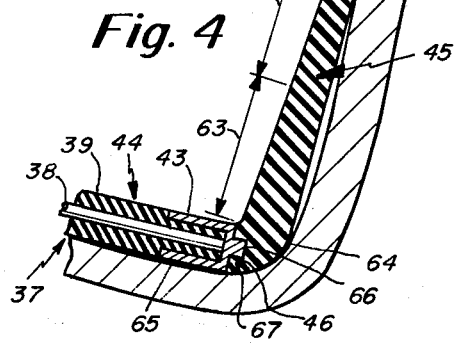
FIG. 4 is a view similar to FIG. 3 showing another embodiment of the invention having a soft, bendable, elbow joint base portion flexing into a generally right angular curve without piercing the wall while the electrode rests in the apex.

In the embodiment shown in FIG. 4, the guide 45 is also of generally "rattail" elongated, uniformly tapered configuration with a hard pointed tip zone 61 and with increasing softness, bendability and flexibility in zone 62, back to the base zone 63 which, while not necessarily of reduced diameter to form a neck, does form an elbow joint 64 because of its greater yieldability and bendability. The electrode 65 is of the cap type with an integral metal post 66 around which the base 67 of the guide is affixed.

In operation an elongated, tapered guide 45 is affixed in forward extension of the exposed electrode 43 of an endocardial lead 37 and the hard guide 45 inserted in a vein in the conventional manner, for threading therealong into the chamber 31 of the right ventricle. Such insertion and threading is much easier than would be the case if the conventional ball tip was in the lead with no tapered guide. The hard pointed tip 47 eases insertion into a vein while not interfering with the bendability of the elbow joint.

Upon passage into chamber 31 the flexible resilient, tapered guide engages the wall 33 and instead of piercing the wall, the guide is gently curved into a generally right angular curl with the tip 47 about mid-height of the chamber and the exposed electrode 43 resting in the apex 32 which is its most desirable location. The right angular configuration of the guide 45 tends to prevent pull out or displacement of the electrode while the endocardial lead 37 and pacemaker 34 are secured in the skin pocket of the wearer.

The integral tapered guide preferably should have a very small diameter tip such as about 2 mm in diameter, the thickness increasing progressively from the 2 mm through 3mm, 4mm, 5mm up to about 6mm at the electrode, and the bendability being most pronouned at the electrode to induce a right angular bend thereat. The most apt description of the guide of the invention is that it looks like, and flexes like a rattail, with an "elbow joint" at the base proximate the exposed electrode.

I claim:

1. A uni-polar endocardial lead, for connection to a cardiac pacemaker to electrically stimulate the heart, said lead comprising:
    an elongated, flexible tube of non-electrically conductive material, substantially inert to body fluids and tissue, having a length of electrically conductive, flexible wire extending therethrough, one end of said wire electrically connected to said pacemaker and the other end of said wire being connected to an exposed electrode;
    and an elongated, tapered integral guide of resilient, flexible non-conductive material in forward extension of said exposed electrode, and of generally "rattail" configuration with a free terminal tip;
    said guide having a base portion, proximate its joinder to said exposed electrode, of high bendability and flexibility to form an elbow joint between said electrode and the remainder of said guide to permit said guide to curl, or bend, at approximately ninety degrees when said tip engages a wall within said heart.

2. A uni-polar, endocardial lead as specified in claim 1 wherein:
    said guide of rattail configuration is of predetermined cross sectional area tapering from said tip rearwardly toward said electrode with progressively increasing diameter to proximate said electrode and having a neck of reduced diameter, at said electrode, to form said base portion, or "elbow joint," of high bendability.

3. A uni-polar, endocardial lead as specified in claim 1 wherein:
    said guide is normally linear and of predetermined softness, and bendability from the tip thereof back to proximate said exposed electrode but the base portion thereof, at said exposed electrode, is of greater softness and of increased bendability and flexibility to yield and bend in the manner of an elbow joint with little tendency to resiliently rebound back to its original linear configuration.

4. A uni-polar, endocardial lead as specified in claim 1 wherein:
    said elongated tapered guide is of predetermined softness and bendability to easily conform to a generally right angular curled configuration when said tip engages a barrier but a predetermined, relatively short zone of said tip, at the free terminal end thereof, is of increased hardness and resistance to bend to permit easy insertion thereof in a vein.

5. An endocardial lead, of the type comprising a silicone tube sleeved around a tantalum wire, the tantalum wire having a free terminal exposed electrode, said lead characterized by:
    an elongated, flexible, resilient, tapered, guide of non-conductive material extending forwardly from said electrode, said guide having a freely bendable elbow joint adapted to flex into generally right angle configuration upon contacting a barrier.

6. An endocardial lead as specified in claim 5 wherein:
    said guide is of solid material, and tapers from said electrode in a gradually decreasing cross-sectional area, and a gradually increasing bendability for a distance of at least one inch beyond said electrode and said elbow joint is formed by a neck of reduced diameter at said electrode.

7. An endocardial body implantable uni-polar lead characterized by having an elongated tapered guide, of resilient, flexible, non-conductive, inert, material integral with, but in front of, the exposed conductive electrode of said lead;
    said guide being of generally "rattail" configuration but having elbow joint means of reduced diameter, forming a freely bendable neck, at said electrode for bending into substantially a right angle upon engaging a wall of a chamber of the heart to avoid piercing said wall and assisting in securing said electrode in the apex of said chamber against inadvertent slidable withdrawal therefrom.

8. The method of securing the exposed electrode of a uni-polar body implantable lead in the ventricle chamber of the heart which comprises the steps of:
    affixing a tapered, flexible, resilient, non-conductive guide of generally rattail configuration to the exposed electrode of said lead to extend in front of said electrode;

inserting said lead in a vein leading to the heart, with said elongated, tapered guide leading the conductive exposed electrode of said uni-polar lead; and upon the tip of said guide engaging a wall of said heart, bending said tapered flexible resilient, non-conductive guide at its base at a right angle to form a curve engaging the wall of the right ventricle chamber near the apex thereof;

whereby said lead has a lessened tendency to pull out of said chamber and no tendency to pierce the wall of said chamber.

* * * * *